United States Patent
Grenz et al.

(10) Patent No.: US 8,663,580 B2
(45) Date of Patent: Mar. 4, 2014

(54) DRIED BIOLOGICAL FLUID SPOT PUNCH DEVICE AND RELATED METHODS

(75) Inventors: Robert Lee Grenz, Santa Ana, CA (US); William C. Hudson, Tustin, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 511 days.

(21) Appl. No.: 12/916,834

(22) Filed: Nov. 1, 2010

(65) Prior Publication Data
US 2012/0103421 A1  May 3, 2012

(51) Int. Cl.
*B01L 3/00* (2006.01)
(52) U.S. Cl.
USPC ............................. 422/527; 422/534; 422/535
(58) Field of Classification Search
USPC ............ 422/405, 401, 420, 68.1, 69, 70, 500, 422/501, 519, 527, 534, 535; 436/174, 180, 436/177, 178; 73/61.53, 61.55, 61.59, 73/61.68, 64.56
See application file for complete search history.

(56) References Cited

U.S. PATENT DOCUMENTS

| | | | |
|---|---|---|---|
| 4,299,812 A | 11/1981 | Coombes | |
| 4,774,192 A | 9/1988 | Terminiello et al. | |
| 4,816,224 A | 3/1989 | Vogel et al. | |
| 5,204,267 A | 4/1993 | Sangha et al. | |
| 5,415,758 A | 5/1995 | Comeau | |
| 5,427,953 A | 6/1995 | Yee | |
| 5,432,097 A | 7/1995 | Yourno | |
| 5,460,057 A | 10/1995 | Ostrup | |
| 5,496,626 A | 3/1996 | Hamajima et al. | |
| 5,508,200 A | 4/1996 | Tiffany et al. | |
| 5,516,487 A | 5/1996 | Rosenthal et al. | |
| 5,906,796 A | 5/1999 | Blevins et al. | |
| 6,048,457 A | 4/2000 | Kopaciewicz et al. | |
| RE36,717 E * | 5/2000 | Thompson | 426/518 |
| 6,176,867 B1 * | 1/2001 | Wright | 606/184 |
| 6,200,474 B1 | 3/2001 | Kopaciewicz et al. | |
| 6,200,533 B1 | 3/2001 | Blevins et al. | |
| 6,416,716 B1 | 7/2002 | Shukla et al. | |
| 6,491,873 B2 | 12/2002 | Roberts et al. | |
| 6,566,145 B2 * | 5/2003 | Brewer | 436/178 |
| 7,595,026 B2 | 9/2009 | Hudson et al. | |
| 7,638,099 B2 | 12/2009 | Lloyd et al. | |
| 2001/0001643 A1 | 5/2001 | Simpson et al. | |
| 2002/0058027 A1 * | 5/2002 | Nelson et al. | 424/94.63 |
| 2006/0057738 A1 * | 3/2006 | Hall, Jr. | 436/177 |

* cited by examiner

*Primary Examiner* — Christopher A Hixson

(57) ABSTRACT

A dried biological fluid spot punch device includes a tube, a frit, and a filter disposed on the frit. The tube includes a main section and a distal section adjoining the main section. The main section includes a proximal tube end circumscribing a proximal tube opening, and the distal section includes a distal tube end circumscribing a distal tube opening. The distal section further includes a distal tube having a tapered inside diameter that reduces from the main section to the distal tube opening. The frit is disposed in the distal section at a distance from the distal tube opening and fixed in position by frictional contact with the distal tube wall. The punch device may also include a punching tool. The punching tool may include a body engaging the tube at the proximal tube end and an ejection mechanism configured for disengaging the body from the tube.

11 Claims, 4 Drawing Sheets

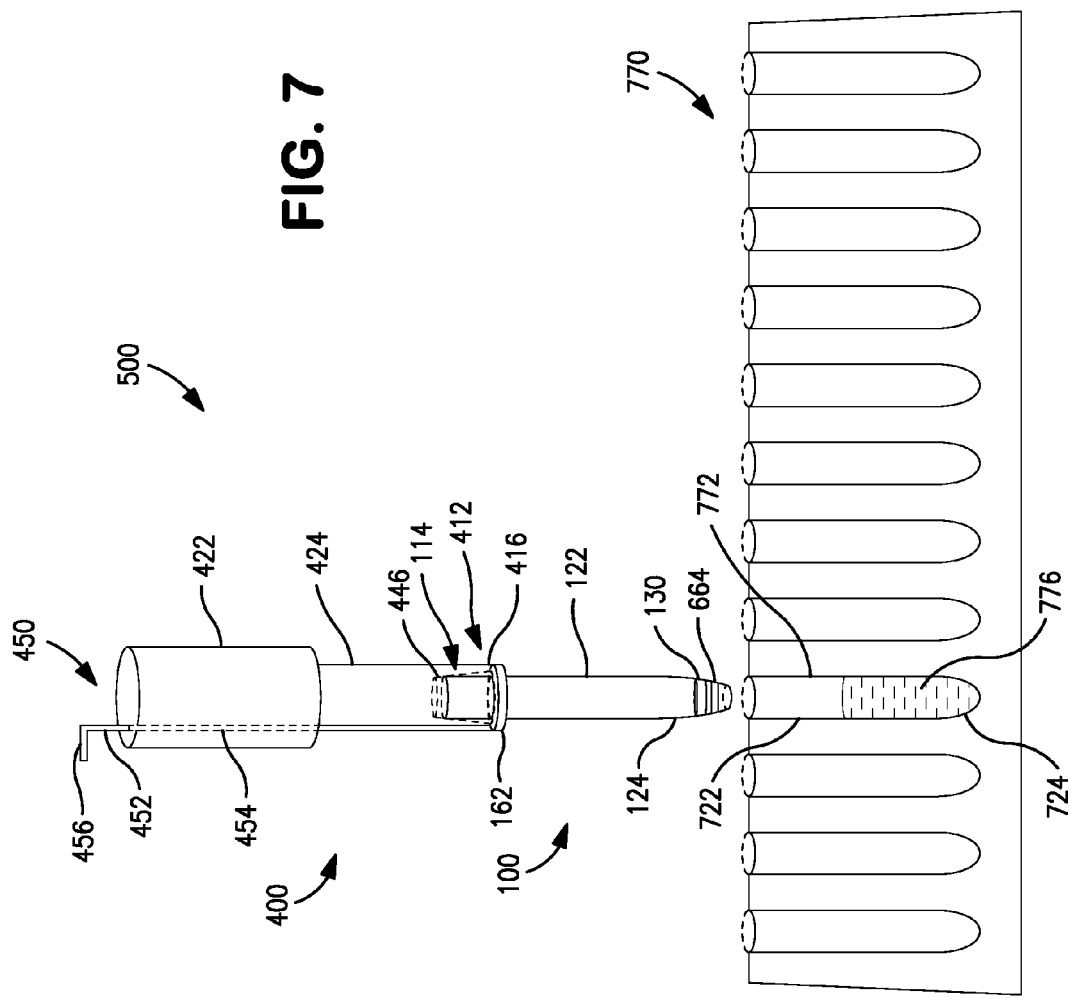

DRIED BIOLOGICAL FLUID SPOT PUNCH DEVICE AND RELATED METHODS

FIELD OF THE INVENTION

The present invention relates generally to dried biological fluid spot analysis and the formation and processing of dried biological fluid spot samples in preparation for subsequent analysis.

BACKGROUND OF THE INVENTION

Dried biological fluid spot analysis such as dried blood spot (DBS) analysis is becoming increasingly popular for pharmaceutical companies in clinical trials. Collection sites for clinical trials may sample blood spots (or other types of biological fluid spots) in the field, allow the spots to dry, and then ship the spots at a lower cost than liquid samples due to the non-biohazard status of dried blood spots and the less rigorous requirements for temperature control. Blood spotting is also becoming useful in preclinical work as analytical chemists are required to store samples for Incurred Sample Reanalysis (ISR) studies, and dried blood spots have proven to be an effective way to stabilize the analytes and the matrix. Typically, DBS samples are prepared by applying drops of blood, typically obtained from venipuncture of a human or animal, to an absorbent substrate (e.g., filter paper) of an appropriate composition. The blood saturates the substrate and is air dried for a period of time (e.g., several hours) sufficient to form an array of circular dried blood spots on the substrate. The spot-containing substrate may then be stored in a plastic container and transported as needed without needing to be frozen. The dried blood spots may thereafter be separated from the bulk substrate by punching the dried blood spots to create individual dried blood spot disks. Analytes such as pharmaceutical compounds, genetic materials, etc. (i.e., small molecules or high molecular weight molecules) may then be extracted from dried blood spots by any number of techniques and subjected to analytical testing. Other types of biological fluid samples may be dried and subsequently processed in an analogous manner.

The processing of dried blood spots and other types of biological fluid spots has many problems. For instance, labs typically utilize a single punching device for multiple sample spotting procedures. Even with the use of cleaning and sterilization procedures, the repeated use of the same punching device can cause carryover and cross-contamination. In addition, the conventional punch device is typically constructed of steel so as to be hard or strong enough to punch through conventional spotting substrates. The steel punching device often must be employed with a hammer to achieve effective punching. Moreover, steel is generally not considered to be readily disposable as compared to other types of materials such as various plastics. Additionally, the procedures of filtration and retention of analytes have conventionally required the use of instruments separate from the punch device. Additionally, the extraction of analytes from a dried biological fluid spot has conventionally required the use of several different components, and typically means for flowing liquid from the punch device to a receptacle such as a multi-well collection plate (e.g., vacuum and/or positive pressure systems). Also, conventional processing of dried biological fluid spots has not been compatible with automated assaying systems.

In view of the foregoing, there is an ongoing need for providing improved apparatus, devices and methods for processing dried biological fluid spots.

SUMMARY OF THE INVENTION

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one implementation, a dried biological fluid spot punch device includes a tube, a fit, and a filter disposed on the fit. The tube includes a main section and a distal section adjoining the main section. The main section includes a proximal tube end circumscribing a proximal tube opening, and the distal section includes a distal tube end circumscribing a distal tube opening. The distal section further includes a distal tube wall having a tapered inside diameter that reduces from the main section to the distal tube opening. The frit is disposed in the distal section at a distance from the distal tube opening and is fixed in position by frictional contact with the distal tube wall. The punch device may also include a punching tool. The punching tool may include a body engaging the tube at the proximal tube end and an ejection mechanism configured for disengaging the body from the tube.

According to another implementation, a dried biological fluid spot punch device includes a tube, a fit, and a filter disposed on the fit. The tube includes a main section and a distal section adjoining the main section. The main section includes a proximal tube end circumscribing a proximal tube opening, and the distal section includes a distal tube end circumscribing a distal tube opening. The distal section further includes a distal tube wall having a tapered inside diameter that reduces from the main section to the distal tube opening. The fit is disposed in the distal section at a distance from the distal tube opening and is fixed in position by frictional contact with the distal tube wall. The tube may be composed of an organic polymer having a Rockwell hardness of 89 or greater.

According to another implementation, a method is provided for acquiring a biological fluid sample from a substrate that includes one or more dried biological fluid spots. A dried biological fluid sample unit is formed. The sample unit includes a portion of the substrate and a selected dried biological fluid spot carried by the portion. The sample unit is formed by operating a tube to punch through the substrate at the portion, separating the sample unit from the substrate, passing the sample unit through a distal opening of the tube, and positioning the sample unit in the tube between the distal opening and a frit of the tube. The tube is inserted into a container until the tube forms a liquid seal with a surface of the container, and such that the distal opening, the sample unit, the frit, and a filter disposed on the frit are submerged in an elution solvent contained in the container. An analyte-inclusive liquid sample matrix is formed above the frit, by maintaining the tube in the container for a period of time sufficient for analytes to be eluted from the sample unit, pass through the filter and the frit, and be carried in the elution solvent at a desired concentration.

According to another implementation, a method is provided for acquiring a biological fluid sample from a substrate that includes one or more dried biological fluid spots. A dried biological fluid sample unit is formed. The sample unit includes a portion of the substrate and a selected dried biological fluid spot carried by the portion. The sample unit is formed by operating a tube to punch through the substrate at the portion, separating the sample unit from the substrate, passing the sample unit through a distal opening of the tube, and positioning the sample unit in the tube between the distal opening and a frit of the tube. The tube is inserted into a container until the tube forms a liquid seal with a surface of the container, and such that the distal opening, the sample unit, the frit, and a filter disposed on the frit are submerged in an elution solvent contained in the container. The filter is configured as a sorbent for analytes, such that analytes eluted from the sample unit are retained on the filter.

According to another implementation, a kit is provided for a dried biological fluid spot punch device. The kit includes a tube, a frit, and a filter. The tube includes a main section and a distal section adjoining the main section. The main section includes a proximal tube end circumscribing a proximal tube opening, and the distal section includes a distal tube end circumscribing a distal tube opening. The distal section further includes a distal tube wall having a tapered inside diameter that reduces from the main section to the distal tube opening. The frit is configured to be disposed in the distal section at a distance from the distal tube opening and fixed in position by frictional contact with the distal tube wall. The filter is configured to be disposed on the frit. The kit may also include a punching tool. The punching tool may include a body configured for engaging the tube at the proximal tube end and an ejection mechanism configured for disengaging the body from the tube.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

FIG. 7 is an elevation view of the tube with the captured dried biological fluid sample unit and the punching tool, and also illustrating the tube and the punching tool held over a multi-well plate and in alignment with a selected well of the multi-well plate.

DETAILED DESCRIPTION OF THE INVENTION

In the context of the present disclosure, the term "fluid" refers generally to liquid-phase materials and gas-phase materials, unless a liquid-phase material or a gas-phase material is specifically indicated. The terms "liquid-phase" and "liquid," and "gas-phase" and "gas," are used interchangeably. A liquid-phase material or liquid may be any liquid, such as a solution, suspension, slurry, multi-phase mixture or the like, and may include gaseous components (e.g., bubbles) and/or solid components (e.g., particles). A gas-phase material or gas may be any gas or vapor, and may include liquid components (e.g., droplets) and/or solid components (e.g., particles). A "dried fluid sample" or a "dried fluid spot" refers generally to a material that was initially provided in the liquid phase and was thereafter dried, such as by air drying.

In the context of the present disclosure, the term "analyte" refers generally to any sample molecule of interest—that is, a molecule on which an analysis is desired such as, for example, a chromatographic analysis.

In the context of the present disclosure, the term "sample matrix" refers to any combination of analytes and non-analytes. The combination of analytes and non-analytes may exist in a liquid phase and/or a gas phase. "Non-analytes" in this context refer to components of the sample matrix for which analysis is not of interest because such components do not have analytical value and/or impair the analysis of the desired analytes. Examples of non-analytes may include water, oils, or other media in which the desired analytes may be found, molecules not of interest, as well as solvents, buffers, reagents, and various solid particles such as excipients, precipitates, fillers, and impurities.

In the context of the present disclosure, the term "diameter" refers in a general sense to the characteristic dimension of any shape and therefore does not necessarily imply a circular shape. As examples, the characteristic dimension of a tube of circular cross-section may be considered a diameter, the characteristic dimension of a tube of elliptical cross-section may be considered a major axis, and the characteristic dimension of a tube of polygonal cross-section may be considered the length (width) of a side or the distance between two inside corners. For convenience, the term "diameter" encompasses all such types of characteristic dimensions.

Figure 1:
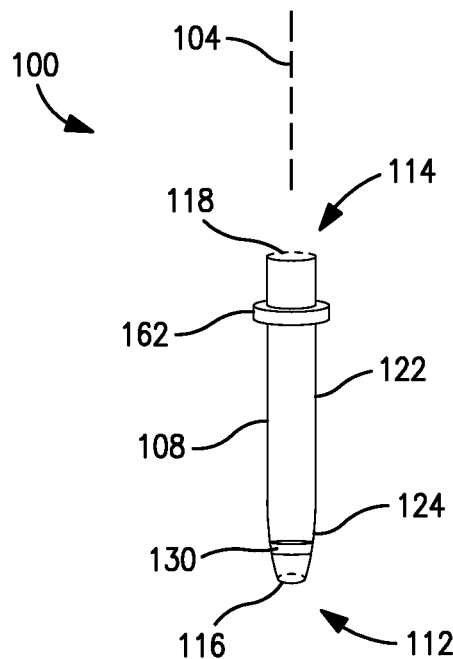
FIG. 1 is an elevation view of an example of a tube according to an implementation of the present teachings.

FIG. 1 is an elevation view of an example of a tube (or pipette, etc.) 100 according to an implementation of the present teachings. The tube 100 is generally situated along a longitudinal axis 104. In FIG. 1 and in typical implementations, the tube 100 has a generally straight orientation along the longitudinal axis 104, while in other implementations the tube 100 may include one or more curved or angled sections. The tube 100 generally includes a hollow body 108 coaxial with the longitudinal axis 104. The hollow body 108 may include a single tube wall or two or more adjoined walls. The hollow body 108 defines an internal cross-sectional area which, from the perspective of FIG. 1, is orthogonal to the longitudinal axis 104. The cross-sectional area may be circular as in the illustrated example, or alternatively may be elliptical or polygonal. The tube 100 (i.e., the hollow body 108) terminates at a distal tube end 112 and an axially opposite proximal tube end 114. The distal tube end 112 circumscribes a distal tube opening 116, and the proximal tube end 114 circumscribes a proximal tube opening 118. In typical implementations, the inside diameter of the distal tube opening 116 is less than the inside diameter of the proximal tube opening 118.

The tube 100 further includes a main section 122 and an adjoining distal section (or pipette tip 124). The main section 122 extends from the distal section 124 to the proximal tube opening 118, and the distal section 124 extends from the main section 122 to the distal tube opening 116. The inside diameter of the distal section 124 tapers in the axial direction from the main section 122 to the distal tube opening 116. Hence, the inside diameter of the distal tube opening 116 is less than the inside diameter of the tube 100 at the point where the main section 122 adjoins the distal section 124. The main section 122 may or may not have a constant cross-sectional area throughout its axial length. That is, the inside diameter of the proximal tube opening 118 may or may not be equal to the inside diameter of the tube 100 at the point where the main section 122 adjoins the proximal section 124.

The tube 100 encloses a volume extending along the longitudinal axis 104 from the proximal tube opening 118 to the distal tube opening 116. In typical implementations, the volume ranges from 100 µL to 5,000 µL (5 mL), while in other implementations the volume may be less than 100 µL or greater than 5 mL. In one non-limiting example, the volume is 700 µL. In typical implementations, the inside diameter of the distal tube opening 116 ranges from 1 to 6 mm. In some implementations, the inside diameter of the distal tube opening 116 ranges from 3 to 4 mm. As described in more detail below, in some implementations the tube 100 is intended for insertion into the well of a multi-well plate (or other type of container). In such implementations, the outside diameter of the tube 100 (at least that portion of the tube 100 intended for insertion into the well) should be slightly less than the inside diameter of the well into which the tube 100 is to be inserted. In typical multi-well plates, the inside diameter of each well ranges from 3 mm to 8 mm.

The tube 100 further includes a frit/filter assembly or composite 130. The frit/filter assembly 130 is fixed in position in the distal section 124 so as to span the cross-sectional area of the distal section 124. In the illustrated example, the frit/filter assembly 130 is fixed in position via frictional contact (or press-fit) with the tapered inside surface of the distal section 124. Hence, one way of installing the frit/filter assembly 130 is to load the frit/filter assembly 130 into the tube 100 at the proximal tube opening 118, and then utilize any suitable tool to urge the frit/filter assembly 130 into frictional contact with the distal section 124 in a transverse orientation relative to the longitudinal axis 104. In typical implementations, the frit/filter assembly 130 is held in place at an axial distance from the distal tube opening 116 ranging from 1 to 5 mm.

Figure 2:
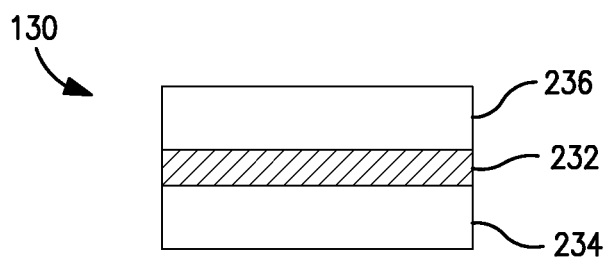
FIG. 2 is a cross-sectional elevation view of an example of a frit/filter assembly according to one implementation, which may be installed in the tube illustrated in FIG. 1.

FIG. 2 is a cross-sectional elevation view of an example of a frit/filter assembly 130 according to one implementation. The frit/filter assembly 130 includes a filter 232 and one or more frits 234, 236. The composition and mesh (or pore) size of the filter 232 generally depend on its function. The filter 232 functions to block the passage of particulates of a desired size range. In some implementations, the filter 232 may also function to retain analytes (or non-analytes) such as by adsorption in a manner analogous to solid phase extraction (SPE) or chromatography. Accordingly, examples of the composition of the filter 232 include, but are not limited to, various organic polymers (homopolymers, copolymers, or polymer blends), glass fiber cellulose, silica, ion exchange modified silica, C8, C18, amide, amino, diol, and combinations of two or more of the foregoing. In some implementations, the filter is composed of a glass fiber matrix that includes (e.g., is embedded with) a bonded phase such as a metal oxide or metalloid oxide. The metal oxide or metalloid oxide is typical one that is capable of reacting with silanes, such as alkoxysilanes, aminosilanes, hydroxysilanes or halosilanes. Examples of suitable metal oxides and metalloid oxides include, but are not limited to, silica, alumina, zeolite, mullite, zirconia, vanadia or titania, and mixtures or composites thereof. The metal oxide or metalloid oxide may functionalized (chemically treated) by a functional moiety. Examples of functional moieties include, but are not limited to, hydrocarbyl (e.g., $C_{2-30}$ alkyl, alkenyl, alkynyl), —NHC(O)— (amido), —C(O)NH— (carbamyl), —OC(O)NH— (carbamato), —NHC(O)O— (urethane), —NHC(O)NH— (carbamido or urea), —NCO (isocyanato), —CHOHCHOH— (diol), $CH_2OCHCH_2O$— (glycidoxy), —$(CH_2CH_2O)_n$— (ethoxy), —$(CH_2CH_2CH_2O)_n$— (propoxy), —C(O)— (carbonyl), —C(O)O— (carboxy), $CH_3C(O)CH_2$— (acetonyl), —S— (thio), —SS— (dithio), —CHOH— (hydroxy), —O— (ether), —SO— (sulfinyl), —$SO_2$— (sulfonyl), —$SO_3$— (sulfonic acid), —$OSO_3$— (sulfate), —$SO_2NH$—, —$SO_2NMe$— (sulfonamido), —NH—, —NMe—, —$NMe_2^+$—, —$N[(CH_2)_n]_2^+$— (amino), —CN (nitrilo), —NC (isonitrilo), —CHOCH— (epoxy), —NHC(NH)NH— (guanidino), —$NO_2$ (nitro), —NO (nitroso), and —$OPO_3$— (phosphate), where Me is methylene or methyl, and where n is an integer up to 30, typically less than 10.

The mesh size of the filter 232 typically ranges from 0.2 µm to 0.45 µM. Although not specifically shown in FIG. 2, the fit 234, 236 may have any porous configuration. The fit 234, 236 is included to provide structural support for the filter 232 while allowing fluid to pass through the frit 234, 236. The filter 232 may be attached or otherwise supported by the frit 234, 236 in any suitable manner. In the example illustrated in FIG. 2, the filter 232 is sandwiched between two frits 234 and 236. When installed in the tube 100 (FIG. 1), at least the lower fit 234 makes frictional contact with the tapered inside surface of the distal section 124. The filter 232 may also make frictional contact with the tapered inside surface but typically needs at least one fit 234 or 236 for additional support. The fit 234, 236 and the tube 100 may have any suitable inert (i.e., non-reactive and non-binding) composition, particularly an organic polymer. In the present context, the term "polymer" encompasses homopolymers, copolymers, and polymer blends. Examples of suitable polymers include, but are not limited to, polypropylene, polyethylene, other polyolefins, polyamide, polyacrylate, a combination of two of more of the foregoing, and more generally any chemically inert plastic formable into a tube or frit such as by injection molding or other suitable fabrication technique. Generally, such polymers may be considered to be inexpensive and readily disposable as compared to steel and other metals. In some implementations, the tube 100 has an inert polymer composition such as just specified, and further the polymer is one which is hard enough to enable a user to effectively punch through a substrate 560 (FIG. 5) of various compositions and thicknesses (examples of which are noted below) without failure of the tube 100. In some implementations, the tube 100 is an inert polymer having (exhibiting) a Rockwell hardness of at least 89 (ranging from 89 or greater) as measured by the Rockwell hardness test R, American Society for Testing and Materials (ASTM) method D785-08 (2008). In one specific yet non-limiting example, the tube 100 is composed of polypropylene of a formulation having a Rockwell hardness of 89.

Figure 3:
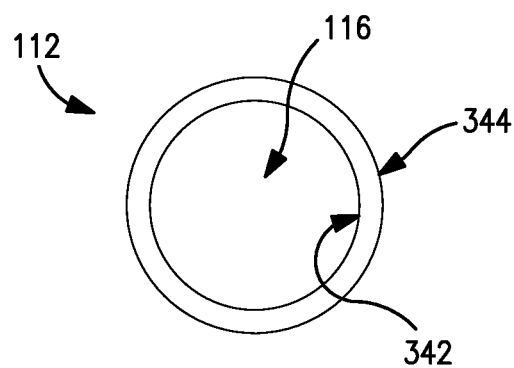
FIG. 3 is a plan view of a distal tube end of the tube illustrated in FIG. 1.

The tube 100 is utilized as a punch device as well as a filter device. Hence, the distal tube end 112 is configured for punching through substrates having compositions and thicknesses contemplated for the tube 100. The distal tube end 112 may be characterized as being "sharp" enough to punch through substrates of interest. FIG. 3 is a plan view of the distal tube end 112. One way to describe the sharpness of the distal tube end 112 is in terms of the thickness of the tube 100 (i.e., the distal tube wall) at the distal tube end 112, i.e., the thickness between an inner surface 342 and an outer surface 344 of the tube 100 at the distal tube end 112. In some implementations, the thickness of the tube 100 at the distal tube end 112 (the distal tube wall) ranges from 0.5 mm or greater, such as 0.5 mm to 8 mm. In other implementations, the thickness of the tube 100 at the distal tube end 112 may range from 2 mm to 8 mm. In some implementations, the outer surface 344 (and thus the outside diameter) of the tube 100 may taper outwardly from the distal tube end 112 in the direction of the longitudinal axis 104 (FIG. 1), in a manner analogous to the tip of a hollow needle.

In some implementations, the thickness of the tube 100 tapers down to a sharp edge at the distal tube end 112, such that the thickness of the sharp edge is less than 0.5 mm. As an example, the distal section 124 may include a first section and a second section adjoining the first section. The second section axially extends from the first section to the distal tube end 112. The first section has a thickness (between the inner surface 342 and the outer surface 344 of the tube 100) of at least 0.5 mm (i.e., the first section thickness is 0.5 mm or greater) or other range as described above in conjunction with FIG. 2, at least at the location where the first section adjoins the second section. The second section is configured such that the distal section 124 of the tube 100 terminates at a sharp edge (i.e., the distal tube end 112 is sharp), which facilitates the use of the tube 100 as a punch tool for a spotting substrate 560. This sharpness may be implemented as follows. The second section has a thickness that tapers down to the distalmost edge of the distal tube end 112. Hence, the thickness of the second section at the distal tube end 112 is less than the thickness of the first section, i.e. is less than 0.5 mm. The tapering of the first section may be implemented by the outer surface 344 of the portion of the distal section 124 comprising the first section being oriented at a greater angle relative to the axis of the distal section 124 than the remaining (upper) portion of the distal section 124. In some implementations, the first section has an angle ranging from 20° to 50° relative to the axis. In another implementation, the angle of the first section is 30° relative to the axis. A further example of a sharp distal tube end 112 is disclosed in FIG. 2B and related description of a U.S. patent application filed concurrently herewith, titled APPARATUS FOR PUNCHING AND SOLID PHASE EXTRACTION OF DRIED BIOLOGICAL FLUID SPOT AND RELATED METHODS, Ser. No. 12/917,138, which is incorporated by reference herein in its entirety.

Figure 4:
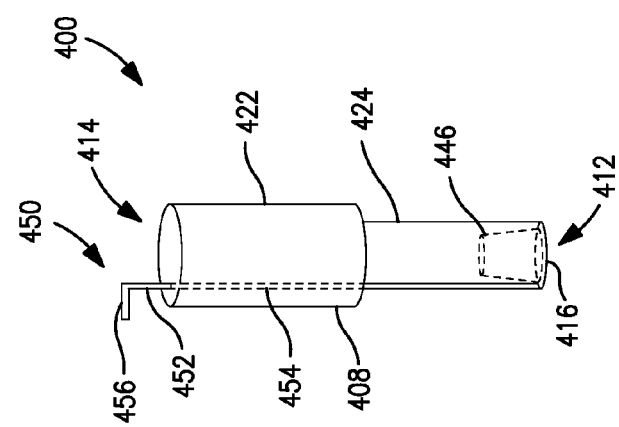
FIG. 4 is an elevation view of an example of a punching tool that may be utilized in conjunction with the tube illustrated in FIG. 1 according to some implementations.

FIG. 4 is an elevation view of an example of a punching tool 400 that may be utilized in conjunction with the tube 100 according to some implementations. The punching tool 400 generally includes a body 408 that terminates at a distal tool end 412 and an axially opposite proximal tool end 414. The body 408 may be cylindrical as illustrated or may have any other shape. The body 408 or a portion thereof may be sized large enough to facilitate manual manipulation by a user. In the illustrated example, the body 408 includes a lower portion 424 and an upper portion 422 of larger outside diameter than the lower portion 424. The punching tool 400 is configured for assisting a user in utilizing the tube 100 to punch through substrate material, such as by providing enhanced mechanical leverage and/or a larger device to grasp. The punching tool 400 is also configured for enabling the user to utilize the tube 100 as a punch without requiring the user to physically handle the tube 100 itself. To these ends, the punching tool 400 may be configured for attachment to the tube 100 and detachment from the tube 100 by any suitable means. In the illustrated example, a tapered (e.g., frusto-conical) bore 446 (i.e., defined by a tapered inner surface) is formed in the lower portion 424 of the punching tool 400 and opens at a distal tool opening 416 circumscribed by the distal tool end 412. The distal tool opening 416 is the maximum inside diameter of the tapered bore 446 and is larger than the outside diameter of the proximal tube end 114 (FIG. 1).

The punching tool 400 may further include an ejection mechanism 450 configured for detaching the punching tool 400 from the tube 100. In the illustrated example, the ejection mechanism 450 is supported by the punching tool 400 and movable into contact with the tube 100. In the illustrated example, the ejection mechanism 450 includes a shaft 452 that moves within and is supported by a bore 454 formed through at least a portion of the body 408 of the punching tool 400. For example, the bore 454 may open at the thickness of the distal tool end 412 between the distal tool opening 416 and an outside surface of the distal tool end 412, and extend through the lower portion 424 and upper portion 422 of the punching tool 400. The shaft 452 may extend beyond the proximal tool end 414 and terminate at or be connected to a tab 456 or other component that facilitates manipulation by a user. The shaft 452 may or may not be spring-loaded (not shown). The shaft 452 may be located or shaped so as to engage or contact any part of the tube 100. In the illustrated example, the distal end of the shaft 452 is located to contact a surface of the tube 100 that protrudes outwardly in the transverse direction. The surface may be provided by a flange or annular shoulder 162 as illustrated in FIG. 1, although it will be understood that the shoulder 162 need not fully surround the tube 100. Attachment of the punching tool 400 to the tube 100 and detachment of the punching tool 400 from the tube 100 in accordance with this example are described below.

Figure 5:
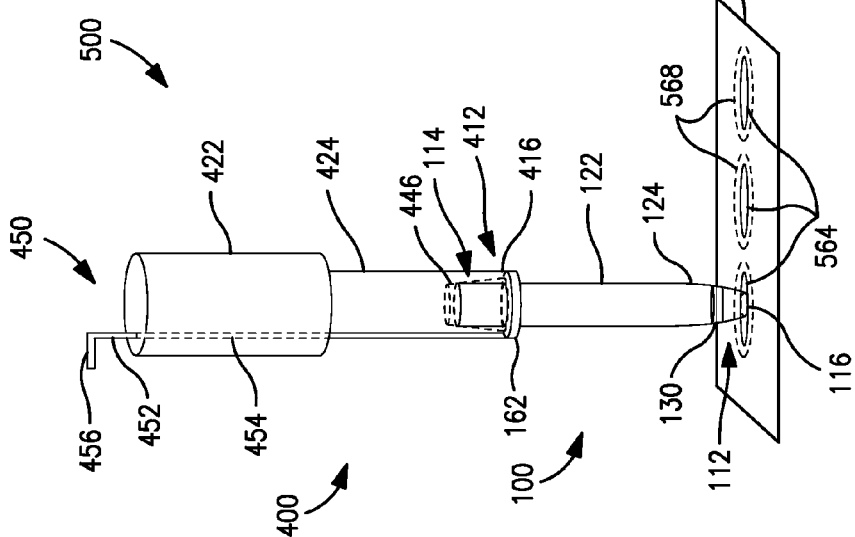
FIG. 5 is an elevation view of the punching tool illustrated in FIG. 4 attached to the tube illustrated in FIG. 1, and also illustrates an example of a substrate containing one or more spots of dried biological fluid.

FIG. 5 is an elevation view of the punching tool 400 attached to the tube 100. To effect attachment, the tube 100 may be initially supported in a fixed position by a rack or other support structure (not shown). The distal tool end 412 is lowered around the proximal tube end 114 and pushed downward until the tapered bore 446 is urged into frictional contact with the proximal tube end 114, thereby securing the punching tool 400 to the tube 100. The tube 100 and the punching tool 400 as assembled together comprise a dried biological fluid spot punch device (or punch/filter device) 500. At this time, a user may handle and transport the punch device 500 by grasping the punching tool 400 without needing to touch the tube 100. A method for detaching the punching tool 400 from the tube 100 (i.e., disassembling the punch device 500) according to this example is also evident from FIG. 5. While the punch device 500 is supported in the well of a multi-well plate (or other support structure), a user grasps the tab 456 and the body 408 of the punching tool 400 and pushes the tab 456 downward until the distal end of the shaft 452 comes into contact with the shoulder 162 of the tube 100. As the user continues to push downward on the tab 456, the shaft 452 is urged against the shoulder 162 until the frictional contact between the tapered bore 446 and the proximal tube end 114 is overcome, at which time the punching tool 400 may be easily removed from the tube 100. In the illustrated example, the tapered bore 446 and the proximal tube end 114 are sized such that at the point of frictional contact the distal tool end 414 rests on the shoulder 162. It will be appreciated, however, that contact between the distal tool end 414 and the shoulder 162 is not required. That is, the shoulder 162 may be located at a distance below the distal tool end 414 so long as the shaft 452 is able to travel far enough to be urged into forcible contact with the shoulder 162.

FIG. 5 also illustrates an example of utilizing the punch device 500. The punch device 500 is held over a substrate (or card, etc.) 560 in which one or more spots 564 of dried biological fluid have been formed. Examples of biological fluids that may be formed into dried spots 564 using the substrate 560 include, but are not limited to, blood-based samples such as whole blood, plasma or serum. In these cases, the spot-containing substrate 560 is often termed a dried blood spotting card. It will be appreciated, however, that biological fluids formable into dried spots 564 are not limited to blood-based samples. The substrate 560 may be composed of any composition suitable for use as a spotting card, non-limiting examples of which include various types of cellulosic filter papers, glass fiber/cellulose composites, cellulose-free glass fiber paper, polyamides (e.g., nylon), propylene, nitrocellulose, polyethersulfone, etc. In some implementations, the substrate material has a composition and thickness suitable for enabling a tube 100 of an inert polymer composition and hardness (as given by examples above) to be manipulated by a user to effectively punch through the substrate 560 to create a dried biological sample unit 664 (FIG. 6, described below) suitable for further processing. That is, in some implementations the substrate material is of the type that does not require the use of a punch device of steel or other metallic construction. This type of substrate material may be considered as being a "soft" material relative to the "hard" polymer of the tube 100, and thus will typically have a Rockwell hardness value of less than 89 (and in advantageous implementations significantly less than 89). Examples of soft substrate materials suitable for sample spotting include, but are not limited to, cellulose-free glass fiber paper and other materials of similar hardness and therefore capable of being punched by a polymer tube 100 of Rockwell hardness of 89 or greater. The thickness of the soft substrate 160 may range from 0.010 inch to 0.050 inch (0.25 mm to 1.3 mm). Preferably, the substrate material is able to uniformly absorb a biological fluid sample to form a homogeneous circular spot 564. Indicia 568 such as dashed circles may be provided on the substrate 560 for assisting in placement of multiple biological fluid samples when it is desired to form an array of dried biological fluid spots 564. The indicia 568 may be printed matter; perforations or scoring are not required in the use of the punch device 500.

Figure 6:
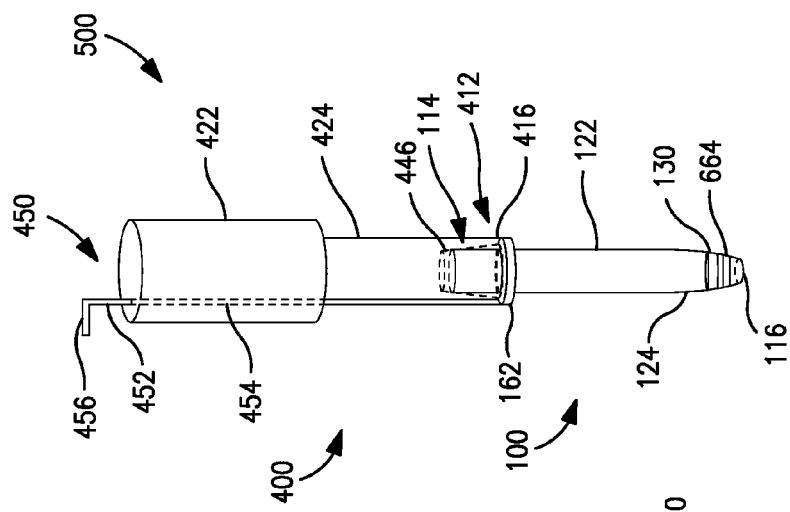
FIG. 6 is an elevation view of the tube and the punching tool after a dried biological fluid sample unit has been punched from the substrate and captured in a distal section of the tube.

To form a dried biological fluid sample unit 664 (FIG. 6), the substrate 560 is supported by any suitable means, the punch device 500 (and particularly the distal tube end 112) is aligned with a selected dried biological fluid spot 564, and the punch device 500 is thrust downward into the selected dried biological fluid spot 564 and through the portion of the substrate 560 containing the selected dried biological fluid spot 564. As the distal tube end 112 is pushed into the material of the substrate 560 and begins to cut the material, the as-forming sample unit 664 is bent upwards and into the distal section 124 of the tube 100. In this manner, a sample unit 664 of greater diameter (or other characteristic dimension) than the distal tube opening 116 eventually separates from the substrate 560 and fully passes through the distal tube opening 116 and into the distal section 124. The shape of the sample unit 664 will depend on the shape of the distal tube end 112. In a typical example in which the distal tube end 112 is circular, the is shaped as a disk. FIG. 6 is an elevation view illustrating the punch device 500 after the sample unit 664 has been formed and captured in the distal section 124. After fully passing through the distal tube opening 116, the sample unit 664 spreads or springs outward and becomes lodged against the inner surface of the distal section 124 by frictional contact, at an axial location between the frit/filter assembly 130 and the distal tube opening 116. The sample unit 664 may be fixed in position in this manner at an axial distance below the frit/filter assembly 130, or may abut the underside of the frit/filter assembly 130. At this time, the punch device 500 with the captured sample unit 664 may be transported to an analytical device or any other desired destination.

FIG. 7 is an elevation view of the punch device 500 with the captured sample unit 664 held over a multi-well plate 770 and in alignment with a selected well 772 of the multi-well plate 770. The multi-well plate 770 may be a standard-format plate utilized for collecting liquid sample such as, for example, a 48-well, 96-well, or 384-well plate. Alternatively, the plate may be a single-well plate or equivalent structure (e.g., a sample vial, cuvette, container, etc.). The plate 770 may be configured for use in conjunction with an automated liquid handling apparatus. In a typical implementation suitable for use in conjunction with the punch device 500, each well 772 includes a constant-diameter section 722 leading to a tapered bottom section 724, which may be analogous to the profile of the tube 100 of the punch device 500. In the illustrated example, the selected well 772 is partially filled with a volume 776 of elution solvent. The volume 776 of the elution solvent is sufficient for creating an analyte-laden liquid sample matrix above the frit/filter assembly 130 (as described below), with the analyte-laden liquid sample matrix having a volume sufficient for aspirating a desired number of aliquots from the tube 100 for subsequent analysis. The type of solvent utilized for elution generally depends on the type of analytes to be eluted from the sample unit 664. Examples of elution solvents include, but are not limited to, methanol, acetonitrile, ethanol, ethyl acetate, methyl tert-butyl ether, dichloromethane, chloroform, and water. It will be appreciated that two or more wells 772 may be utilized in conjunction with two or more punch devices 500, either simultaneously or sequentially. Two or more wells 772 may contain different elution solvents, and two or more punch devices 500 may likewise contain respective sample units 664 of different compositions.

Figure 8:
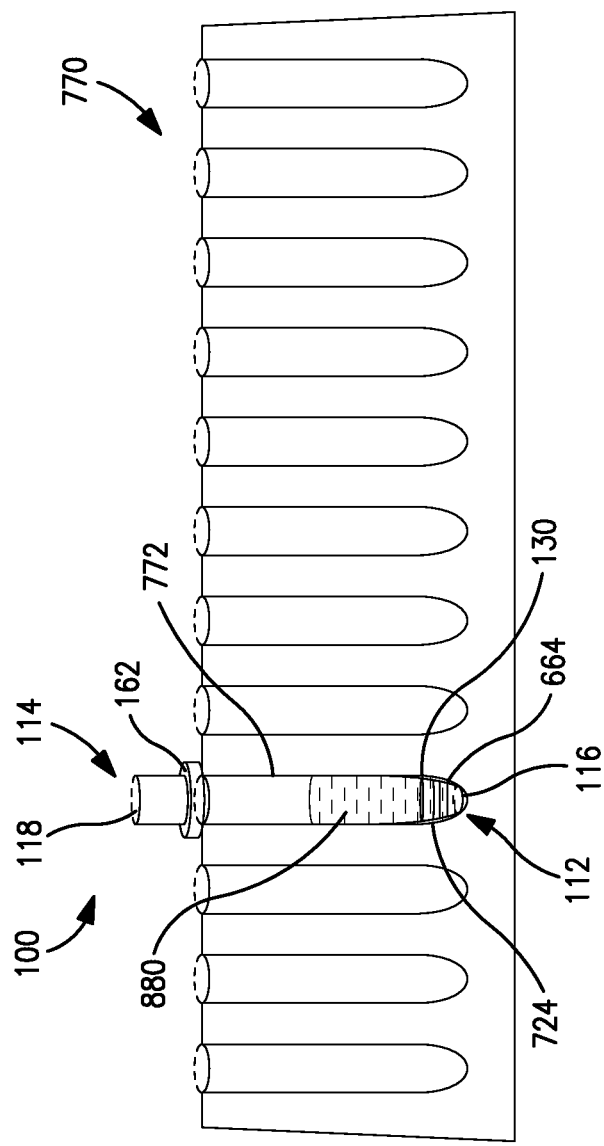
FIG. 8 is an elevation view of the tube inserted in the selected well illustrated in FIG. 7.

According to one implementation, the punch device 500 may be utilized in conjunction with the multi-well plate 770 or other type of container as part of a method for acquiring a biological fluid sample from a substrate 560 (FIG. 5) containing one or more dried biological fluid spots 564. In the method, a dried biological fluid sample unit 664 is formed and captured by the punch device 500 in the manner described above. The punch device 500 is then transported to the multi-well plate 770 and positioned over a selected well 772 containing an elution solvent as shown in FIG. 7 (or over a container not forming a part of a multi-well plate). The punch device 500 is then inserted into the selected well 772 or container until a liquid seal is formed between the tube 100 of the punch device 500 and the well 772 or container. As an example, FIG. 8 is an elevation view illustrating the tube 100 inserted in the selected well 772. As noted above, the tube 100 is sized to snuggly fit into the well 772. In this example, the tube 100 is inserted into the well 772 until the distal tube end 112 comes into frictional contact with the inner surface of the tapered bottom section 724 of the well 772, thereby establishing a liquid-tight seal. The punching tool 400 (FIG. 7) may then be detached from the tube 100 in the manner described above. It will be appreciated that while FIG. 8 illustrates the shoulder 162 of the tube 100 resting on the top surface of the multi-well plate 770, this is not a requirement of the present teachings.

While the tube 100 is being inserted into the well 772, the elution solvent is displaced and flows upward through the distal tube opening 116, passing through the dried biological fluid sample unit 664, the frit(s) and the filter of the frit/filter assembly 130, whereby a significant volume of the elution solvent is located above the frit/filter assembly 130. The filter prevents non-analytical particulates or precipitates of the captured biological fluid sample unit 664, and any freed pieces of the substrate component of the sample unit 664, from passing through the filter. Some particulates or precipitates may settle to the bottom of the well 772 or remain as suspended solids below the frit/filter assembly 130. As time passes, analytes of the biological fluid are eluted from the sample unit 664 and pass through the frit/filter assembly 130 to the liquid volume above the frit/filter assembly 130, thus creating an analyte-inclusive liquid-phase sample matrix or supernatant 880 above the frit/filter assembly 130. A sufficient period of time is permitted to transpire to create a sample matrix 880 having a concentration of analytes sufficient for subsequent analysis. The period of time will vary for different types of analytes and associated elution solvents. In a typical example for blood-based matrices and certain other biological component-based matrices, the period of time may range from 1 min to 48 hours.

After creating the analyte-inclusive liquid sample matrix 880, the analyte-inclusive liquid sample matrix 880 may be processed in any desired manner for separating, concentrating, purifying, and/or analyzing the analytes (i.e., subsequent analytical techniques). Examples of subsequent analytical techniques include, but are not limited to, protein precipitation, fraction collection, centrifugation, spectrophotometry, nuclear magnetic resonance (NMR) spectrometry, various types of SPE (e.g., normal-phase, reversed-phase, ion-exchange, etc.), and various types of chromatography (e.g., preparative chromatography, liquid chromatography (LC), gas chromatography (GC), etc.) as well as hyphenated techniques entailing mass spectrometry (LC/MS$^n$, GC/MS$^n$, etc.). Other subsequent analytical techniques include the testing or processing of genetic material (i.e., "genetic testing") such as ribonucleic acid (RNA) or deoxyribonucleic acid (DNA). Examples of genetic testing include, but are not limited to, polymerase chain reaction (PCR), reverse transcriptase PCR (RT-PCR), ligase chain reaction (LCR), hybridization, genomic sequencing, labeling, assaying, etc. When the multi-well plate 770 is utilized, the multi-well plate 770 may be placed in a liquid handling robot for automated subsequent analysis, as appreciated by persons skilled in the art. Alternatively, the liquid sample matrix 880 may be aspirated from the tube 100 and injected directly into an analytical instrument (e.g., LC, GC, LC/MS$^n$, GC/MS$^n$, etc.). The tube 100 of the punch device 500, or both the tube 100 and the punching tool 400, may be discarded after use.

As noted above, in some implementations the filter 232 (FIG. 2) of the tube may have a composition appropriate for utilizing the filter 232 as a sorbent in a manner analogous to a solid or stationary phase material utilized in SPE or chromatographic procedures. For example, the material of the filter 232 may be configured for retaining certain analytes eluted from the sample unit 664. Analytes retained by the filter 232 may subsequently be collected by, for example, thermal or solvent-based desorption. Alternatively, the filter 232 may be configured for retaining certain non-analytical material that might otherwise pass through the filter 232 and into the liquid sample matrix 880 being formed above the frit/filter assembly 130. The non-analytical material may be any chemical or biological species not of interest to the user, and generally depends on the type of biological fluid sample and/or the analysis to be performed. Examples of non-analytical material may thus include components considered to be interferences, ion suppressing components, salts, surfactants, lipids, proteins, etc. Filters 232 configured with adsorption material may be utilized to improve the sensitivity of subsequent analytical procedures, and more generally may be utilized in the development of a diverse variety of methods.

It will be understood that the punching tool 400 is not required in all implementations. Accordingly, in some implementations the punch device 500 includes the tube 100 and the punching tool 400, while in other implementations the punch device 500 includes the tube 100 only.

In some implementations of the present disclosure, a dried biological fluid punch/filter kit is provided. The kit may include one or more tubes 100, one or more frits 234, 236, and one or more filters 232, examples of which are described above. The tube(s) 100 may be disposable, i.e., configured for single-use. In the case of a kit providing two or more tubes 100, the tubes 100 may each have the same dimensions and shape and thus be configured for use in conjunction with a specific type of multi-well plate 770 or other collection device. Alternatively, the tubes 100 may have different dimensions and/or shapes such that the kit is compatible with more than one type of multi-well plate 770 or other collection device. Likewise, in the case of a kit providing two or more filters 232, the filters 232 may have the same or different mesh sizes and/or compositions depending on a desired range of applications contemplated for the kit. The kit may provide the frit(s) 234, 236 and filter(s) 232 separately or as one or more preassembled frit/filter assemblies 130. The kit may provide a frit/filter assembly 130 separately from a tube 100 or pre-installed in the tube 100. In some implementations, the kit may include a punching tool 400 as described above for subsequent attachment to the tube 100 by a user. In some implementations, the kit may include tangible media (printed matter, computer-readable storage media, etc.) providing instructions for assembling the punch device 500, utilizing the punch device 500 according to one or more methods, etc.

One or more implementations of the punch device 500 and related methods disclosed herein provide one or more of the following features, advantages, or improvements. The punch device 500 may be utilized in a wide variety of dried biological sample spot analyses of pharmaceutical compounds, other drug-related compounds, or other chemistries, or high molecular weight (HMW) molecules such as DNA, RNA, proteins or other polymers. Such analyses include dried blood spot analyses as noted above. The punch device 500 provides an effective, reliable technique for punching various types of spot-containing substrates. The punch device 500 optionally includes a punching tool 400 that allows a user to utilize the tube 100 of the punch device 500 without physically handling the tube 100 itself. The punch device 500 is configured for use with a wide variety of readily available collection devices such a standard multi-well plates, and thus is readily adapted for automated sample filtration/cleanup and analysis. The punch device 500 is configured for creating liquid sample matrices from dried biological fluid spots without the need for vacuum-applying equipment, positive pressure-applying equipment, gaskets or other types of fluid seals, or other costly components. The punch device 500 may be fabricated entirely of disposable materials, thereby significantly limiting carryover and cross-contamination.

In general, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A dried biological fluid spot punch device, comprising:
a tube comprising a main section and a distal section adjoining the main section, wherein the main section comprises a proximal tube end circumscribing a proximal tube opening, the distal section comprises a distal tube end circumscribing a distal tube opening, and the distal section further comprises a distal tube wall having a tapered inside diameter that reduces from the main section to the distal tube opening, wherein the distal tube end comprises a sharp edge and hardness effective for punching through a substrate on which the dried biological fluid spot is formed;
a frit disposed in the distal section at a distance from the distal tube opening and fixed in position by frictional contact with the distal tube wall;
a filter disposed on the frit; and
a punching tool comprising a body engaging the tube at the proximal tube end and an ejection mechanism configured for disengaging the body from the tube.

2. The dried biological fluid spot punch device of claim 1, wherein the distal tube opening has a diameter ranging from 1 to 6 mm.

3. The dried biological fluid spot punch device of claim 1, wherein the distance of the frit from the distal tube opening ranges from 1 to 5 mm.

4. The dried biological fluid spot punch device of claim 1, wherein the frit is one of at least two frits, and the filter is interposed between the at least two frits.

5. The dried biological fluid spot punch device of claim 1, wherein at least one of the tube, the punching tool, and the frit has a composition selected from the group consisting of an organic polymer, an organic copolymer, and an organic polymer blend.

6. The dried biological fluid spot punch device of claim 1, wherein at least one of the tube, the punching tool, and the frit has a composition selected from the group consisting of polyolefins, polypropylene, polyethylene, polyamide, polyacrylate, or a combination of two of more of the foregoing.

7. The dried biological fluid spot punch device of claim 1, wherein the tube comprises an organic polymer having a Rockwell hardness of 89 or greater.

8. The dried biological fluid spot punch device of claim 1, wherein the filter has a composition selected from the group consisting of an organic polymer, an organic copolymer, an organic polymer blend, a glass fiber cellulose, a metal oxide or metalloid oxide, an ion exchange modified metal oxide or metalloid oxide, a functionalized metal oxide or metalloid oxide, and combinations of two or more of the foregoing.

9. The dried biological fluid spot punch device of claim 1, wherein the ejection mechanism comprises a shaft movably supported by the body and movable into contact with the tube.

10. The dried biological fluid spot punch device of claim 1, wherein the body comprises a distal body end, the distal body end comprises a tapered inside wall circumscribing a bore, the bore has an inside diameter at the distal body end greater than an outside diameter of the proximal tube end, and the body engages the proximal tube end by frictional contact between the proximal tube end and the tapered inside wall of the distal body.

11. The dried biological fluid spot punch device of claim 10, wherein the main section comprises an outer surface and a shoulder extending from the outer surface, and the ejection mechanism comprises a shaft movably supported by the body and movable into contact with the shoulder.

* * * * *